(12) United States Patent
Greenberg et al.

(10) Patent No.: US 8,659,409 B2
(45) Date of Patent: Feb. 25, 2014

(54) IN-VEHICLE DISPLAY FOR IMPROVING FUEL ECONOMY

(75) Inventors: Jeff Allen Greenberg, Ann Arbor, MI (US); Dean Mengel, Livonia, MI (US); Les R. Bodnar, Dearborn, MI (US); Sonya Nematollahi, Rochester Hills, MI (US); Finn Tseng, Ann Arbor, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 120 days.

(21) Appl. No.: 13/356,663

(22) Filed: Jan. 24, 2012

(65) Prior Publication Data

US 2012/0123665 A1 May 17, 2012

(51) Int. Cl.
*B60Q 1/00* (2006.01)
*G06F 19/00* (2011.01)

(52) U.S. Cl.
USPC ........... 340/439; 340/438; 340/441; 340/461; 701/110

(58) Field of Classification Search
USPC ........... 340/439, 438, 441, 461, 442–450, 47, 340/457.1, 457.2, 457.3, 457.4, 463–468, 340/488, 425.5, 815.4, 815.45; 701/1, 22, 701/110; 362/23.01, 612; 180/167, 65.21; 903/902; 73/114.52, 114.53, 514.37, 73/514.36
See application file for complete search history.

(56) References Cited

U.S. PATENT DOCUMENTS

| | | | | |
|---|---|---|---|---|
| 4,151,751 A | * | 5/1979 | McCaslin | 73/514.37 |
| 4,246,778 A | * | 1/1981 | Fiala | 73/114.52 |
| 5,463,370 A | * | 10/1995 | Ishikawa et al. | 340/439 |
| 2005/0280521 A1 | * | 12/2005 | Mizumaki | 340/438 |

* cited by examiner

*Primary Examiner* — Ahn V La
(74) *Attorney, Agent, or Firm* — Joseph E. Root

(57) ABSTRACT

A visual feedback system for a vehicle including an engine, includes an operating control for varying the engine's speed. Connected to the engine, an engine acceleration reporter reports an amount of acceleration of the engine. A creation control being linked to both the engine acceleration reporter and the operating control enables the creation of images on a visual display according to a variation in the engine speed. Accordingly, the creation control creates a pendulum image within a sector of a circle, with the pendulum image swinging in response to the amount of acceleration being reported by the engine acceleration reporter.

14 Claims, 4 Drawing Sheets

IN-VEHICLE DISPLAY FOR IMPROVING FUEL ECONOMY

FIELD OF THE INVENTION

This application relates generally to the field of improvements in vehicular fuel economy, and more particularly to systems for training drivers to achieve improved fuel economy.

BACKGROUND

Modern transportation, running on non-renewable fuels, faces a challenge from depleting fuel reserves, rising fuel costs, and tighter emission norms. Such challenges have led to an increased awareness among vehicle owners and manufacturers of the need to conserve energy resources, causing excessive fuel consumption in vehicles to be a major concern that needs to be addressed.

Many of the factors contributing to excessive fuel consumption are related to the total weight of the vehicle, engine capacity, engine or vehicular design, etc. One aspect of excessive fuel consumption, however, lies in an individual's driving behavior, which is often overlooked.

An individual's driving pattern may vary over time and may periodically cause excessive throttle movement and improper braking during acceleration or deceleration maneuvers, respectively. Such a condition may not only cause discomfort to the vehicle's occupants, but may also contribute significantly to excessive fuel consumption, leading to the depletion in the vehicle's fuel supply.

Currently, quantities of training materials and modules for training drivers are available on the internet and in other media. None of these materials, however, teaches an efficient way of controlling the throttle and brake pedals to improve fuel economy. Smooth throttle control and steady braking are teachable skills that can be learned with the correct course of instruction.

Room for improvement thus exists to teach and train a driver to improve her fuel efficiency. One solution lies in a real time driver coaching or teaching method, and it would accordingly be desirable to have a driver's training system, which is operated from within vehicular confines. Such a system would enable real time learning, consequently leading to improvements in the vehicle's overall fuel economy.

SUMMARY

One embodiment of the present application describes a visual feedback system for a vehicle. The vehicle includes an internal combustion engine connected to an operating control enabling engine speed variations, and an engine acceleration reporter that reports an amount of acceleration of the engine. A creation control being connected to both the operating control and the engine acceleration reporter, creates visual images on a visual display according to variations in the engine acceleration. The creation control accordingly creates a pendulum image within a sector of a circle, on the visual display. The pendulum image is configured to swing in response to the amount of acceleration of the engine reported by the engine acceleration reporter.

Another embodiment of the present application discloses a method for improving fuel economy in a vehicle during an acceleration maneuver. The vehicle includes an internal combustion engine, and the method comprises activating an in-vehicle visual feedback system. The method further includes, accelerating and varying the speed of the engine through an operating control. Further, an engine acceleration reporter reports an amount of acceleration of the engine and displays a change in the amount of acceleration on a visual display through a creation control. Subsequently, the creation control being connected to the operating control and to the engine acceleration reporter, creates a pendulum image within a sector of a circle, with the pendulum image swinging in response to the amount of the engine's acceleration reported by the engine acceleration reporter.

BRIEF DESCRIPTION OF THE DRAWINGS

The figures described below set out and illustrate a number of exemplary embodiments of the disclosure. Throughout the drawings, like reference numerals refer to identical or functionally similar elements. The drawings are illustrative in nature and are not drawn to scale.

DETAILED DESCRIPTION

The following detailed description is made with reference to the figures. Exemplary embodiments are described to illustrate the subject matter of the disclosure, not to limit its scope, which is defined by the appended claims.

Overview

In general, the present disclosure describes methods and systems for an in-vehicle system to improve fuel economy while driving. To this end, the system employs a visual display as part of the system. The visual display is connected to an operating control of the vehicle, causing a graphical representation of variations in the operating control, during a vehicular maneuver, to be displayed. The variations being depicted are in the form of a pendulum that sweeps an area in the form of a sector of a circle, having defined portions for efficient acceleration and deceleration maneuvers, the maneuvers consuming optimum fuel. Inefficient portions are also defined for the area swept, depicting consumption of excessive fuel during similar acceleration and deceleration maneuvers. An audible feedback may assist in situations when the pendulum crosses over from one portion to the other.

Exemplary Embodiments

Figure 1:
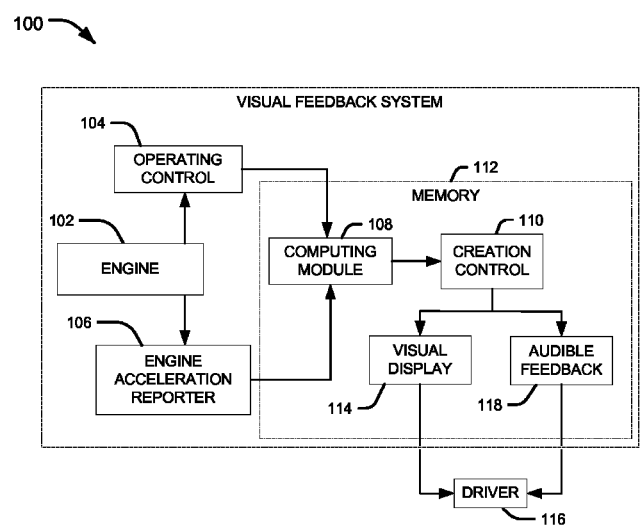
FIG. 1 is a schematic of an exemplary embodiment of an in-vehicle visual display system for improving fuel economy.

FIG. 1 schematically depicts an exemplary in-vehicle visual feedback system 100. The system 100 generally includes an internal combustion engine 102 connected to an operating control 104, the operating control 104 configured to control the engine's operation by increasing or decreasing the engine's speed. An engine acceleration reporter 106 is linked to the engine 102, and is configured to constantly report an amount of acceleration of the engine 102. A creation control 110, being connected to the engine acceleration reporter 106 and the operating control 104 through a computing module 108, provides inputs for a visual display 114. Such inputs enable aspects of the engine's acceleration to be shown to a driver 116 through the creation control 110, which is configured to create visual images. Further, the creation control 110 also includes means for making an audible signal, configured as an audible feedback 118 to complement the visual display 114. A memory 112 to store all preliminary and resultant data is also configured within the system 100, and may be linked to the computing module 108, creation control 110, and the visual display 114. The linkages and connections, noted above, may all be enabled through cables.

The operating control 104 within the system 100 is a unit connected to the engine 102, and configured to cause the engine 102 to vary in speed, and accordingly accelerate and decelerate the vehicle, when required. More particularly, the operating control 104 is configured to be controllable by the driver 116, and may be a device known in the art, such as an accelerator pedal, throttle control units, joysticks, etc. Such devices, because of their wide conventional applications, are known to the ones skilled in the art, and thus will not be discussed further.

Certain proximity or position sensors can be configured, in a conventional manner, in such a way that they sense the operational positions of the operating control 104, and subsequently feed the positional data to the computing module 108.

The engine acceleration reporter 106 is a microprocessor-based device configured to function as a calculating and a reporting unit, calculating an amount of acceleration of the engine 102, and reporting it. The engine acceleration reporter 106 further includes appropriate input and output circuits of a known type for receiving input signals, and for transmitting various commands to the computing module 108. In addition, the engine acceleration reporter 106 is configured to report the acceleration of the engine 102 either constantly, or at specific predetermined intervals, set automatically through a logic sub-system (not shown), or set by the driver 116.

In one embodiment of the present disclosure, speed data sensors may be configured, along with a vehicle's speedometer, to constantly gauge the vehicle's speed. Speed related information observed through such an arrangement could also form raw data for the engine acceleration reporter 106 to calculate the rate of speed. Such rate of speed calculations can be assisted through a timer (not shown) provided with the engine acceleration reporter 106, to thus form inputs and a basis for the calculation and reporting of the vehicle's acceleration. It will be understood that in such an arrangement the engine acceleration reporter 106 need not be linked to the engine 102.

In another embodiment, the functionality of the speed data sensors could be replaced with a tachometer that would measure the engine's rotations per unit time. In addition, the tachometer may also be configured to provide speed related inputs to the engine acceleration reporter 106. Acceleration related information, assisted through the timer, could thus be processed, reported and consequently transmitted to the creation control 110, through the computing module 108.

A fuel gauge (not shown) can also be incorporated into the intake port of the engine 102, and the gauge could constantly monitor and gauge the flow and quantity of fuel entering the vehicle's combustion chamber. Sensing units could accordingly be placed along with the fuel gauge to precisely sense and report fuel flow and quantity. An analysis of the fuel consumed could then be retrieved, and the corresponding data may subsequently be fed directly to the computing module 108. With this data available, the vehicle's fuel economy can be calculated.

The computing module 108, included in the system 100, is a microprocessor based device, and includes one or more processors to process the incoming signals from the operating control 104, the engine acceleration reporter 106, and the fuel gauge. Through the fuel consumption values obtained from the fuel gauge, the computing module 108 is configured to compute values of fuel economy by retrieving calculation methodologies stored in the memory 112. In addition, the computing module 108 is adapted to convert values of the reported acceleration, fuel economy, and position of the operating control 104 into a compatible format. Depiction of such compatible formats of acceleration maneuvers, depending on the position of the operating control 104, in relation to the calculated fuel economy, is thus made possible through a creation control 110 (discussed later). Further, a RAM and/or ROM that functions as a volatile memory unit, along with associated input and output buses, is also configured in the computing module 108, providing for temporary memory and storage functionalities.

As discussed above, the memory 112 in the system 100 is configured to be linked to the computing module 108, creation control 110 and visual display 114, storing and maintaining all calculated values, changeable formats, calculation methodologies, display configurations, audible feedbacks, etc. The memory 112 could further comprise dual potions of volatile or non-volatile memory, enabling both temporary and permanent storage of information.

Since variations in the position of the operating control 104 cause varying consumption of fuel over time, the quantity of fuel being consumed is adapted to be constantly sensed through the fuel gauge. Such constant sensing particularly enables the corresponding fuel economy to be calculated through the computing module 108. The overall fuel economy thus calculated may constantly be updated according to variations in fuel consumption levels resulting from variations in accelerations over time. The constant update of such data is displayed on the visual display 114 through the creation control 110.

Accordingly, the values thus computed of the fuel economy, acceleration and operating control's positions, are configured to form inputs for the creation control 110, which in turn is adapted to process such values and create an image on the visual display 114. The image illustrates a variation in the rate of fuel consumption in a visual range, as compared to a predefined visual range. More particularly, the creation control 110 is a device similar in structure to the computing module 108, and is adapted to process the incoming signals from the computing module 108, converting them to a readable format for the visual display 114. Such conversion is assisted through logic algorithms configured within the creation control 110, which enables the analysis and processing of such raw signals, making them understandable for human perception. Alternatively, an application specific software may be installed on the creation control 110 and configured to read incoming acceleration values, operating control's positions, and fuel economy formats, computed through the computing module 108, to then convert them into a relational simulation. Such simulations are the variation of the image, as noted above, in relation to the predefined visual range. Further, such simulation may be adapted to be understood by the driver 116 when displayed on the visual display 114.

The visual display 114 can be a LCD display or a touch-screen user interface, enabled separately from other vehicular functionalities, or the visual display 114 can be integrated into the already existing in-vehicle driver interfaces, enabled with pre-installed interfaces. Positioned in the instrument cluster, the visual display 114 is configured to be at an optimum viewing distance from the driver 116.

Complementing the visual display 114, the creation control 110 includes provisions for creating audible signals as well. Accordingly, for the audible feedback 118 to be heard by the driver 116, existing speaker outputs within the vehicle may be linked to the creation control 110. The creation control 110, processing the outputs from the engine acceleration reporter 106 and the operating control 104, may be configured to provide inputs to the speakers, which in turn provide the audible feedback 118, configured as an audible signal, as an output. Such outputs obtained through the speakers may be in the form of a tone or a music being played in sync to the visual display 114 or according to variations sensed in the acceleration. Alternatively, some outputs may be configured as a vocal command instructing the driver 116 to modify his driving behavior. Optional provisions may be enabled for the driver 116 to switch between an activated and de-activated audible feedback 118.

The image, as discussed above, is adapted to vary according to a variation in the vehicle's acceleration, the acceleration being controlled by the driver 116 through the operating control 104. The predefined visual range, on the other hand, is the range to be maintained in order to achieve optimum fuel economy during accelerations, the accelerations being positive and negative, i.e. decelerations, as well.

Figure 2A:
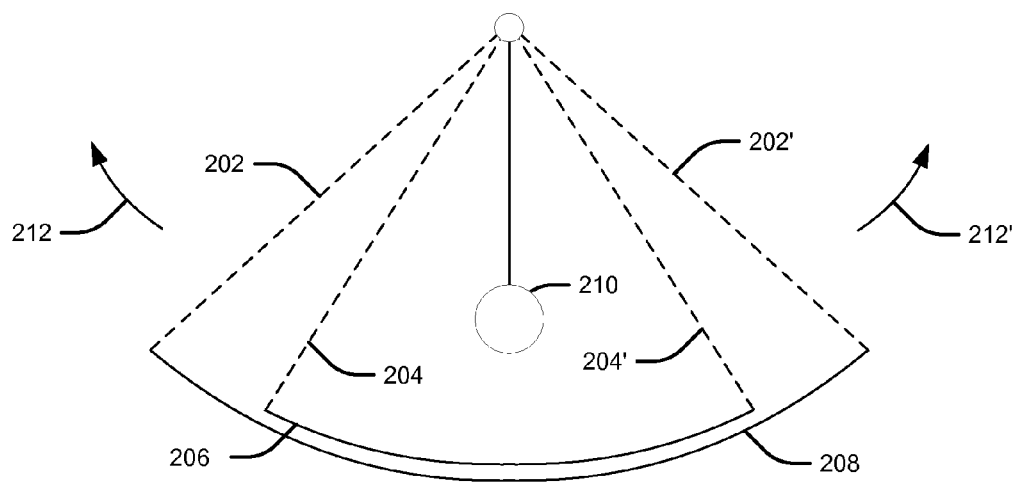
FIG. 2A is an exemplary in-vehicle visual display depicting a pendulum at the center of a sector, when the vehicle has made no acceleration according to the present disclosure.

Conforming to the aspects as noted above, the present disclosure utilizes the image of a pendulum 210, as shown in FIG. 2A. The creation control 110 accordingly, is configured to create the image of a pendulum 210 within a sector of a circle, the sector being a predefined visual range, and covering the swing of the pendulum 210. The pendulum 210 is configured to swing in response to the amount of acceleration of the engine 102, reported by the engine acceleration reporter 106, and swings across the predefined visual range in the visual display 114. Such swinging depicts variations in the accelerations of the engine 102, with the predefined visual range depicting both acceleration and deceleration regions. More particularly, the predefined visual range is a predefined fuel economy range. In the same figure, the two sectors depicted are configured to include a city portion and a highway portion. Accordingly, the smaller sector depicts a city economy range 206, provided with a city acceleration limit 204' and a city deceleration limit 204, and a larger sector that depicts a highway economy range 208 with a highway acceleration limit 202' and a highway deceleration limit 202. Deceleration direction 212 and acceleration direction 212' depict the possible swinging directions for the pendulum 210, respectively depicting deceleration and acceleration.

Particularly, FIG. 2A depicts a condition when the pendulum 210 is at the center of the sectors. This condition is the home position for the operating control 104 and the pendulum 210, and depicts the engine 102 making no accelerations. Correspondingly, the engine acceleration reporter 106 reports no acceleration as well.

Figure 2B:
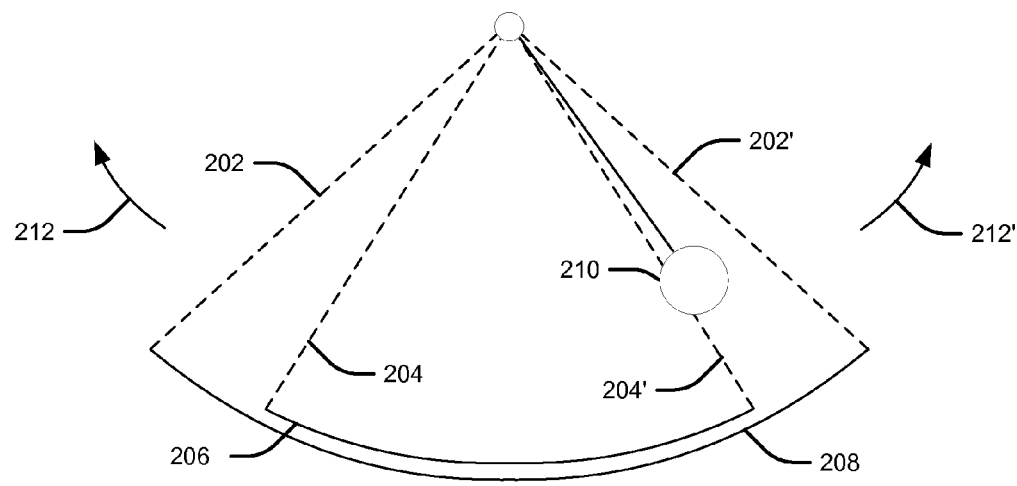
FIG. 2B is an exemplary in-vehicle display depicting a pendulum swinging to the right and the vehicle accelerating in a fuel-efficient range, during highway driving, according to the present disclosure.

FIG. 2B illustrates a condition where the engine 102 has started and the driver 116 has accelerated by varying the operating control 104. The pendulum 210 is shown travelling across the city acceleration limit 204', but falling within the highway acceleration limit 202'. Such a condition depicts acceleration unsuitable for economical running in the city, however favorable for highway driving.

Figure 2C:
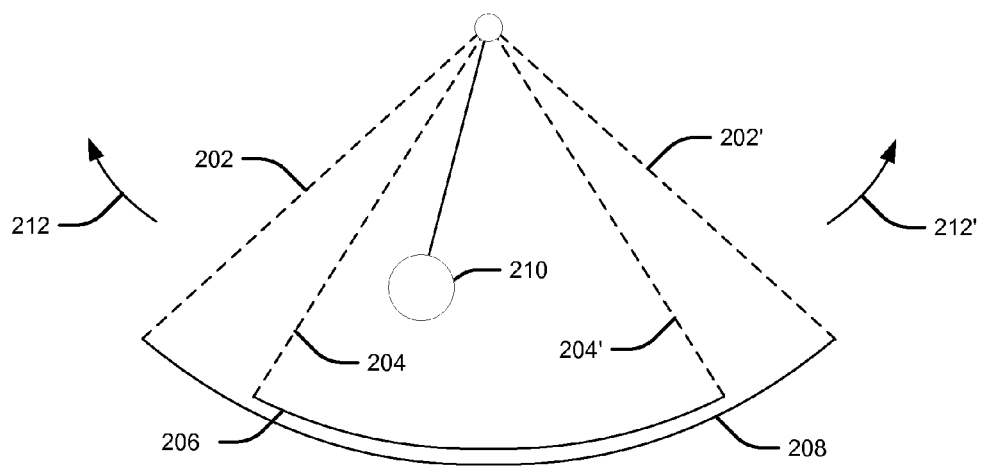
FIG. 2C is an exemplary in-vehicle display depicting a pendulum swinging to the left and the vehicle decelerating within a fuel-efficient range, during city driving, according to the present disclosure.

FIG. 2C is an exemplary embodiment of the system 100 depicting the pendulum 210 traveling in the deceleration direction 212, however falling within both the city economy range 206 and the highway economy range 208, making the condition favorable for both city and highway decelerations.

Figure 2D:
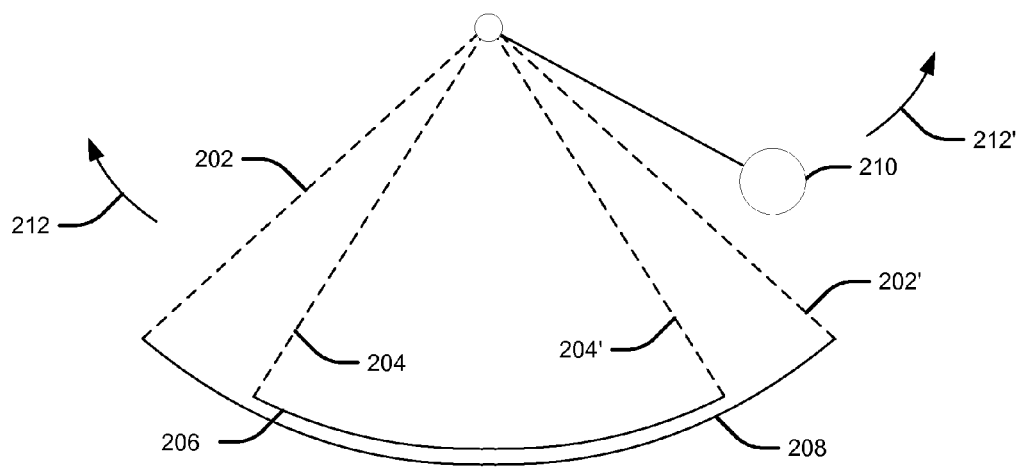
FIG. 2D is an exemplary in-vehicle display depicting a pendulum swinging to the right and the vehicle accelerating beyond a fuel-efficient range according to the present disclosure.

FIG. 2D exemplarily illustrates the pendulum 210 travelling beyond both the city and the highway acceleration limits 204' and 202', making the condition unsuitable for economical driving in both city and on highway. Such a condition may be termed as a hard acceleration. Similarly, the pendulum 210 travelling beyond the city and highway deceleration limits 204 and 202, respectively, during a deceleration maneuver, may equally be uneconomical, and may be termed as a hard deceleration.

With the sectors depicting the predefined fuel economy range, it will thus be understood, that the pendulum 210 is configured to swing outside the sectors of the circle if either the amount of acceleration or deceleration of the engine 102 runs outside the predefined fuel economy range.

The depiction of such variations in the consumption of fuel on the visual display 114 enables the driver 116 to maintain control over the operating control 104 for economical driving. The system 100 thus equips and imparts the driver 116 with better driving capabilities.

Figure 3:
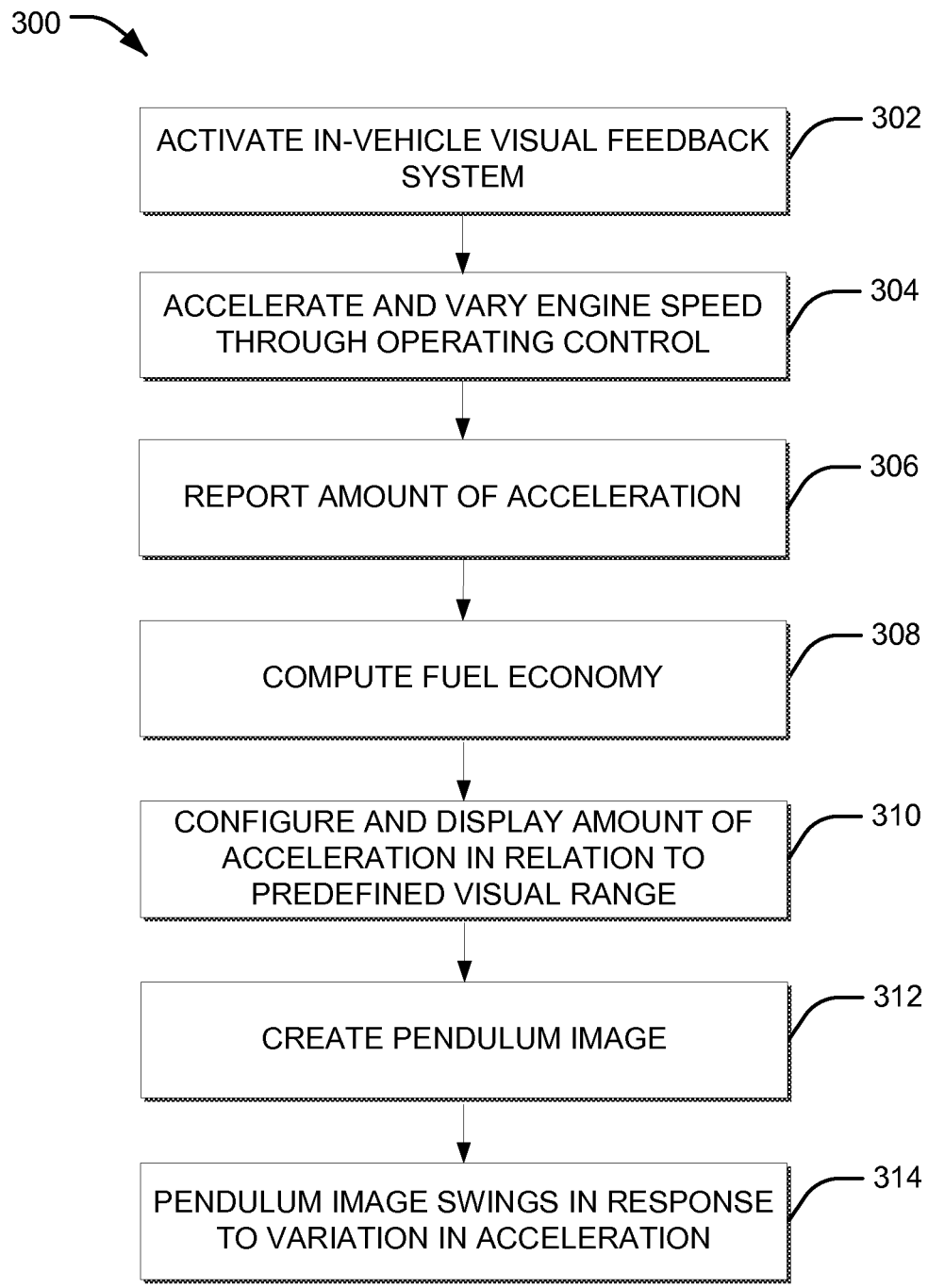
FIG. 3 is a flowchart illustrating an exemplary method for training a driver for fuel economy improvement, according to the present disclosure.

As discussed, the system 100 set out above generates a visual display 114 designed to assist drivers in improving fuel efficiency. The system 100 thus operates according to a methodology 300 depicted in FIG. 3, and is described as follows.

At stage 302, the driver 116 activates the in-vehicle visual feedback system 100. Such activation could be initiated either through a manual input disposed within vehicle confines, or may be initiated automatically at the start of vehicle operation.

Further, the driver 116 accelerates the engine 102 and varies the engine's speed through the operating control 104, at the stage 304. In the following stage 306, the engine acceleration reporter 106 reports an amount of acceleration of the engine 102, the engine acceleration reporter 106 being connected to the engine 102, constantly monitors the acceleration values.

The engine's acceleration data reported through the engine acceleration reporter 106, is fed to the computing module 108. Subsequently, the computing module 108 converts the raw acceleration data into a compatible format, readable by the creation control 110.

A fuel gauge, incorporated with the fuel intake port, constantly monitors and gauges the fuel consumed by the engine 102, further enabling the computing module 108 to calculate a fuel economy value of the engine 102, at the stage 308.

Communicating with the computing module 108, the creation control 110, at stage 310, configures a variation or an amount of acceleration through an image in relation to the predefined visual range, as discussed earlier. The predefined visual range being a predefined fuel economy range is depicted through a sector of a circle. More particularly, at stage 312, the creation control 110 configures to display the image as the pendulum 210 that swings across the sector of a circle. The swing of the pendulum 210 depicting a change in the amount of acceleration of the engine 102, controlled through the operating control 104 by the driver 116, is all carried out in stage 314. The image is accordingly obtained on the visual display 114, configured to be understood by the driver 116, enabling him to develop better driving skills.

Audible feedback 118 can assist in situations when the pendulum 210 crosses over from one sector to another, or when the pendulum image swings outside the sector of the circle, enabling the driver 116 to notice conditions of hard accelerations or hard decelerations without having to observe the visual display 114. Such exemplary feedbacks may be configured as a sound of a bell, vocal commands, a continuous beep tone, with a varying tempo, configured to be directly proportional to variations in the acceleration, etc.

In another embodiment, the system 100 can be configured as a portable unit or a kit, providing for an easy transfer and installation between multiple vehicles.

The specification has set out a number of specific exemplary embodiments, but those skilled in the art will understand that variations in these embodiments will naturally occur in the course of embodying the subject matter of the disclosure in specific implementations and environments. It will further be understood that such variation and others as well, fall within the scope of the disclosure. Neither those possible variations nor the specific examples set above are set out to limit the scope of the disclosure. Rather, the scope of claimed invention is defined solely by the claims set out below.

We claim:

1. A visual feedback system for a vehicle, the vehicle including an internal combustion engine, the system including:
    an operating control for operating the engine to increase and decrease the engine's speed;
    an engine acceleration reporter reporting an amount of acceleration of the engine;
    a visual display; and
    a creation control for creating visual images for the visual display, the creation control being connected to the operating control and to the engine acceleration reporter, the creation control creating a pendulum image within a sector of a circle, the pendulum image swinging in response to the amount of acceleration of the engine reported by the engine acceleration reporter.

2. The system of claim 1, wherein the sector of the circle includes a city portion and a highway portion.

3. The system of claim 1, wherein the pendulum image swings outside the sector of the circle if one of the following occur:
    the amount of acceleration of the engine is outside a predefined fuel economy range; and
    an amount of deceleration of the engine is outside a predefined fuel economy range.

4. The system of claim 1 further including means for making an audible signal, and wherein the audible signal is created by the creation control when the pendulum image swings outside the sector of the circle.

5. The system of claim 1, wherein the pendulum image is centered in the sector of the circle when the engine acceleration reporter reports no acceleration.

6. The system of claim 1, wherein the amount of acceleration is at least one of the following:
    positive; and
    negative.

7. The system of claim 1, wherein the operating control is at least one of:
    an accelerator pedal; and
    a throttle control.

8. A method for improving fuel economy in a vehicle during an acceleration maneuver, the vehicle including an internal combustion engine, the method comprising:
    activating an in-vehicle visual feedback system;
    accelerating and varying a speed of the engine through an operating control;
    reporting an amount of acceleration of the engine through an engine acceleration reporter; and
    displaying a change in the amount of acceleration on a visual display through a creation control, the creation control being connected to the operating control and to the engine acceleration reporter,
    creating a pendulum image within a sector of a circle through the creation control, the pendulum image swinging in response to the amount of acceleration of the engine reported by the engine acceleration reporter.

9. The method of claim 8, wherein the sector of the circle includes a city portion and a highway portion.

10. The method of claim 8, wherein the pendulum image swings outside the sector of the circle if at least one of:
    the amount of acceleration of the engine is outside a predefined fuel economy range; and
    an amount of deceleration of the engine is outside a predefined fuel economy range.

11. The method of claim 8 further including means for making an audible signal, and wherein the audible signal is created by the creation control when the pendulum image swings outside the sector of the circle.

12. The method of claim 8, wherein the pendulum image is centered in the sector of the circle when the engine acceleration reporter reports no acceleration.

13. The method of claim 8, wherein the operating control is at least of:
    an accelerator pedal; and
    a throttle control.

14. The method of claim 8, wherein the amount of acceleration is at least one of:
    positive; and
    negative.

* * * * *